Figure 1:
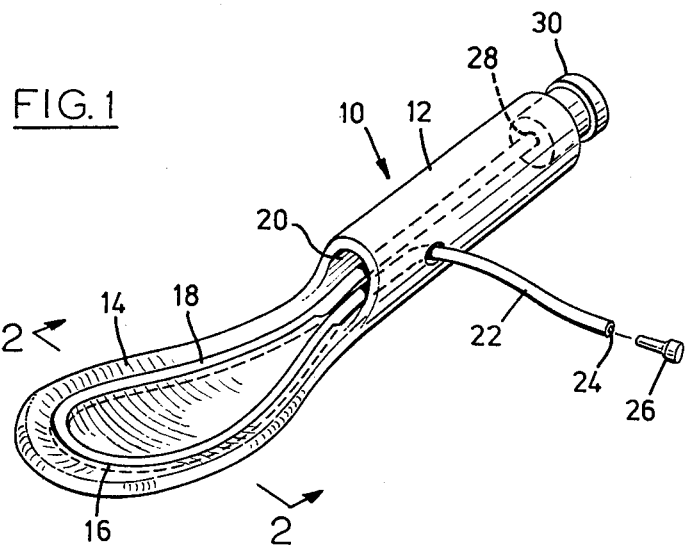

United States Patent [19]

Gallie

[11] 4,327,733
[45] May 4, 1982

[54] CRYOENUCLEATION TOOL

[75] Inventor: Brenda L. Gallie, Toronto, Canada

[73] Assignee: Governing Council of the University of Toronto, Toronto, Canada

[21] Appl. No.: 229,235

[22] Filed: Jan. 28, 1981

[51] Int. Cl.³ ............................................. A61B 17/36
[52] U.S. Cl. ................................. 128/303.1; 128/400
[58] Field of Search ................... 128/DIG. 21, 303.1, 128/303.16, 400; 435/35; 62/293

[56] References Cited

U.S. PATENT DOCUMENTS

| 2,129,987 | 9/1938 | Berkson | 433/35 |
| 3,674,031 | 7/1972 | Weiche | 62/293 |
| 3,712,306 | 1/1973 | Bryne | 128/303.1 |

FOREIGN PATENT DOCUMENTS

| 1512302 | 1/1968 | France | 128/303.1 |
| 1552671 | 11/1968 | France | 128/303.1 |
| 1289103 | 9/1972 | United Kingdom | 128/303.1 |

OTHER PUBLICATIONS

Journal of Cryosurgery, "Affections of the Eyelids Amenable to Cryosurgery", Zacgrian, vol. 1, No. 2, Aug. 1968.

Primary Examiner—Robert W. Michell
Assistant Examiner—J. L. Kruter
Attorney, Agent, or Firm—Hirons, Rogers & Scott

[57] ABSTRACT

A cryoenucleating device is provided for freezing a melanoma tumor in an eyeball and for removing the eyeball. The device comprises a spoon, the bowl of which is formed of thermally insulating material to conform with the contours of an average eyeball. A refrigerating loop is provided, supported in the concavity of the spoon bowl to freeze the tumor while the thickness of the bowl insulates adjacent tissue from freezing.

6 Claims, 2 Drawing Figures

U.S. Patent

May 4, 1982

4,327,733

CRYOENUCLEATION TOOL

FIELD OF THE INVENTION

The invention relates to apparatus for use in freezing a tumor in the eye during surgical procedure.

BACKGROUND OF THE INVENTION

It is now thought that the surgical removal of eyes containing choroidal malignant melanoma has helped the spread of tumor cells to other parts of the patient rather than the intended purpose of removing all the tumor cells to avoid such dissemination. It has been found that pressures within the eye rise dramatically during an enucleation or eye removal. It is believed that such pressures may cause showers of tumor cells into the blood stream of the patient.

In a previous attempt to prevent the possibility of such a release of tumor cells, a device for freezing a tumor in an eye has been developed. This device comprises a loop or tube through which liquid nitrogen is flowed to freeze the tumor and the area surrounding it. The loop may be adjusted to the size of the tumor. When this device is used the first stage of the operation is to surgically enter the eye cavity and separate the eye from connecting tissue until the area of the tumor is reachable. The device is then placed with the loop encircling the tumor and liquid nitrogen is intermittently passed through the loop to maintain a continuous freeze around the tumor. When the tumor is solidly frozen the remaining connective tissue may be separated from the eye and the eye may be lifted from the socket fixed to the loop through which liquid nitrogen flows.

This device causes some difficulty in that there is a tendency for adjacent tissue to freeze causing sticking of the eye to the adjacent orbital contents. It is necessary to protect adjacent structures from freezing with thin, sterilized sheets of styrofoam. Moreover, many tumors of the type which necessitates removal of the eye are located at the back of the eye. If this previously designed device is to be used considerable surgery must be carried out in order to place the freezer loop in a suitable position. The positioning of the loop is sometimes difficult and may, in some cases, be impossible.

SUMMARY OF THE INVENTION

It is an object of the present invention to provide an improved device for freezing a tumor in an eye to avoid dissemination of tumor cells into the patient's circulatory system during removal of the eye.

Accordingly the invention provides apparatus for cryoenucleating a tumor of the eye comprising:
a spoon of thermally insulating material having a handle and a concave bowl and adapted to receive an eyeball,
and a refrigerating loop supported by the concavity of the bowl and adapted to substantially surround a tumor in said eyeball thereby to freeze it, means being provided to circulate refrigerant in passage means of said loop.

SPECIFIC DESCRIPTION OF THE INVENTION

Figure 2:
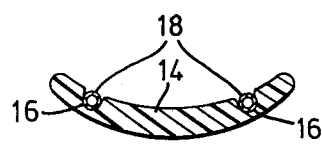

One embodiment of the invention will now be described with reference to the accompanying drawings in which FIG. 1 is a respective view from above of one form of apparatus according to the invention; and FIG. 2 is a section through the spoon shown in FIG. 1.

The cryoenucleation apparatus of the invention, as shown in the drawings, comprises a spoon 10 having a handle 12 and a bowl 14. The spoon 10 including both the handle 12 and the bowl 14 are molded from silicon plastics material which has some flexibility. The bowl is shaped so that its concavity fits the contour of the average eyeball.

On the concave surface of the bowl 14 of the spoon 10 is a recess 16 accepting the loop of silicon plastics material tubing 18 so that the top of the silicon tubing lies flush with the concave surface of the bowl and does not upstand therefrom to form a ridge. One end portion 22 of loop 18 passes for a short distance through a passage 20 which is coaxial within the handle 12. The end portion 22 vents to the atmosphere at opening 24 where an end plug 26 may be provided. The other end portion 28 of the loop 18 passes through the coaxial passage 20 over the whole length of the handle 12 and, where it emerges from the handle 12 is provided with coupling means 30 to connect it to a source of liquid nitrogen. Coupling means 30 may be, for example, a Luer-Lock attaching device.

In use, the bowl 14 of spoon 10 is easily inserted into the Tenon's space and slid behind the eye with the tubing loop lying against the sclera. This loop 18 is carefully positioned to surround the tumor and thereafter liquid nitrogen is permitted to flow through coupling means 30 into end 28 of the tubing and around the loop 18 through end portion 21 to vent to the atmosphere at 24. The tumor and the area surrounding it is thus easily frozen while the bowl of the spoon thermally insulates adjacent tissues from freezing. Using this device it is possible to reach tumors at the back of the eye and freeze them. During freezing it is possible to observe the tumor through the dilated pupil of the eye until it can be seen that sufficient freezing has occurred. Surgery is then completed and the eye is lifted from the socket on the spoon.

I claim:

1. Apparatus for cryoenucleating a tumor of the eye comprising:
    a spoon of thermally insulating material having a handle and a concave bowl and adapted to receive an eyeball,
    and a refrigerating loop supported on the concave side of the bowl and of a size adapted to substantially surround a tumor in said eyeball thereby to freeze it, means being provided to circulate refrigerant in passage means of said loop.

2. Apparatus as claimed in claim 1 in which the spoon is formed from silicon plastics material.

3. Apparatus as claimed in claim 1 in which the refrigerating loop is a tube formed from silicon plastics material.

4. Apparatus as claimed in claim 1 in which the passage means of said loop is adapted to be connected to a source of liquid nitrogen as refrigerant and circulatable in said passage means.

5. Apparatus as claimed in claim 1 in which the loop is located in a recess in the concavity of the spoon bowl.

6. Apparatus as claimed in claim 1 in which a source of refrigerant is connected to the loop by connecting means passing coaxially through the handle of the spoon and refrigerant is vented to the atmosphere from the loop by passage means coaxially passing through the handle of the spoon.

* * * * *